(12) United States Patent
Douglas

(10) Patent No.: US 11,380,065 B2
(45) Date of Patent: Jul. 5, 2022

(54) ADVANCED HEAD DISPLAY UNIT FOR FIRE FIGHTERS

(71) Applicant: Robert Edwin Douglas, Winter Park, FL (US)

(72) Inventor: Robert Edwin Douglas, Winter Park, FL (US)

(73) Assignee: RED PACS, LLC, Winter Park, FL (US)

( * ) Notice: Subject to any disclaimer, the term of this patent is extended or adjusted under 35 U.S.C. 154(b) by 0 days.

(21) Appl. No.: 16/997,830

(22) Filed: Aug. 19, 2020

(65) Prior Publication Data

US 2021/0375053 A1 Dec. 2, 2021

Related U.S. Application Data

(63) Continuation-in-part of application No. 16/936,293, filed on Jul. 22, 2020.

(60) Provisional application No. 62/889,169, filed on Aug. 20, 2019.

(51) Int. Cl.
| | |
|---|---|
| *G06T 19/00* | (2011.01) |
| *G06F 3/01* | (2006.01) |
| *G06F 3/147* | (2006.01) |
| *G06F 3/14* | (2006.01) |
| *G02B 27/01* | (2006.01) |
| *G02B 27/00* | (2006.01) |
| *G06V 20/20* | (2022.01) |

(52) U.S. Cl.
CPC ........ *G06T 19/006* (2013.01); *G02B 27/0093* (2013.01); *G02B 27/0172* (2013.01); *G06F 3/012* (2013.01); *G06F 3/013* (2013.01); *G06F 3/017* (2013.01); *G06F 3/147* (2013.01); *G06F 3/1454* (2013.01); *G06V 20/20* (2022.01); *G02B 2027/0174* (2013.01); *G06T 2219/024* (2013.01)

(58) Field of Classification Search
CPC .......... G02B 27/017; G02B 2027/0138; G02B 27/0093; G06F 3/013; G06F 3/017; G06T 19/006

See application file for complete search history.

(56) References Cited

U.S. PATENT DOCUMENTS

| | | | |
|---|---|---|---|
| 2009/0097710 A1* | 4/2009 | Sroka | G06T 7/74 382/103 |
| 2015/0138613 A1* | 5/2015 | Choo | G03H 1/2202 359/9 |
| 2015/0338915 A1* | 11/2015 | Publicover | G06F 21/316 345/633 |
| 2016/0217614 A1* | 7/2016 | Kraver | G02B 27/017 |
| 2020/0020145 A1* | 1/2020 | Jones | G06F 3/011 |

\* cited by examiner

*Primary Examiner* — Ross Varndell

(57) ABSTRACT

In this patent, an advanced head display unit designed primarily for fire fighters is disclosed. The advanced augmented reality/virtual reality (AR/VR) head display unit improves coordination between teammates through eye tracking coupled with augmented reality features. This allows one fire fighter to know where another fire fighter is looking and helps coordinate tasks by dividing the scene into sectors and visibly marking each sector. Further, this system helps determine where to hose with a smart target system. Further, multiple sensors are utilized together to triangulate the location of a victim's voice. Additional advantages are also disclosed above.

20 Claims, 11 Drawing Sheets

| In some situations, the camera can detect small movements of an item of interest that the human eye does not detect or does not detect very well.<br>634 |

↓

| The HDU display can place a smooth tracking dot in close proximity to a small moving object.<br>636 |

↓

| The smooth tracking dot moves in a continuous fashion so as to help the human eye follow the subtle movement.<br>638 |

Fig. 7A

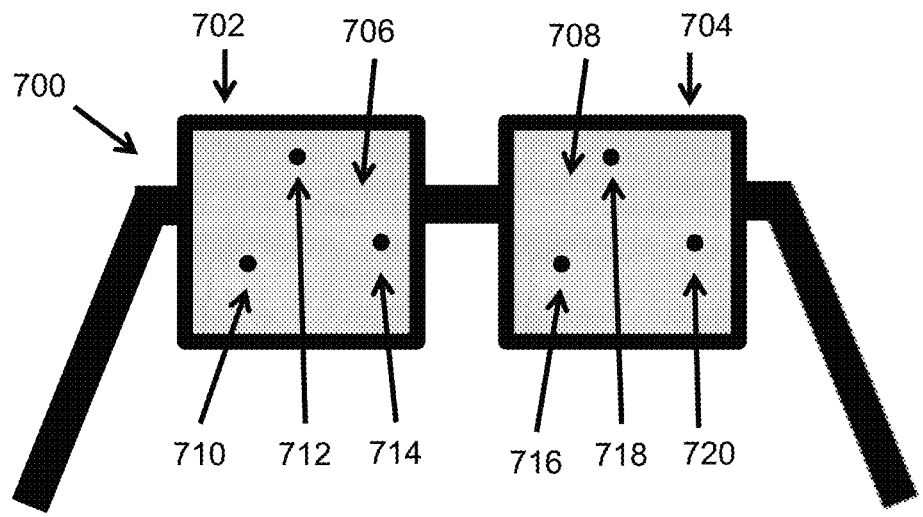

Fig. 7B

Some situations require that multiple objects need to be tracked by a single Fire fighter. And, of course, the Fire fighter is vulnerable to human error and improper sequencing and tracking.
722

The HDU displays a first saccadian visual aid marker at the first object for a first time interval, a second saccadian visual aid marker at a second object during a second time interval. And, so on.
724

The smooth tracking dot moves in a continuous fashion so as to help the human eye follow the subtle movement.
726

ADVANCED HEAD DISPLAY UNIT FOR FIRE FIGHTERS

TECHNICAL FIELD

Aspects are generally related to equipment to aid in fire fighting.

BACKGROUND

Fire fighters perform important duties in a range of complex environments.

SUMMARY

This patent provides a method and apparatus, which improves upon existing fire fighter equipment in several important ways. First, fire fighters who use this innovative technology will have improved coordination and communication amongst multiple team members. Next, fire fighters who use this technology will have improved visualization of subtle features in the field of view. Next, fire fighters will have a visual map of the current and changing heat in the region. Next, artificial intelligence will be utilized to determine the most effective way to take out a target and save victims. All examples, aspects and features mentioned in this document can be combined in any technically possible way.

An Advanced Extended Reality Head Display Unit

The apparatus disclosed enhances a fire fighter's situational awareness during a fire fight. An extended reality display is utilized. This invention therefore comprises a method, an apparatus and a software suite. The preferred embodiment of the extended reality display is an augmented reality headset wherein the user can see both digital images and the real world scene.

Improved Coordination Amongst Team Members

The extended reality display will be equipped with a computer connected to and providing projections on a head mounted display and also connected to a communications system to deliver augmented reality/virtual reality generated data over a tactical communications network comprising. Some embodiments comprise generating and displaying a line on the head display indicating where a fire fighter is looking which line is superimposed on a map, digital photo, etc., and which line is sharable among team members. Some embodiments comprise generating and displaying a line on the head display indicating where the Fire fighter's hose is pointing which line is superimposed on a map, digital photo, etc., and which line is sharable among team members. Some embodiments comprise generating and displaying lines on the head display indicating the Fire fighter sector of fire which lines are superimposed on a map, digital photo, etc., and which line is sharable among team members. Some embodiments comprise generating and displaying lines on the head display indicating the Fire fighter assigned targets for distribution of fires/engagements sector of fire which lines are superimposed on a map, digital photo, etc., and which line is sharable among team members. Some embodiments comprise generating and displaying lines on the head display indicating location of a potential target or victim (e.g., victim) which lines and image are superimposed on a map, digital photo, etc., and which line and image are sharable among team members. Some embodiments comprise generating and displaying lines on the head display indicating where the Fire fighter is looking and also where the hose is pointing which lines are superimposed on a map, digital photo, etc., and which lines are sharable among team members. Some embodiments comprise generating and displaying a cursor which, through Fire fighter interaction with graphical user interface touchpad, can be used to, inter alia, mark targets or persons of interest (e.g., victim). Some embodiments comprise generating and displaying a track box(es) which is superimposed on a victim, target or object which, through image processing, and/through Fire fighter interaction with graphical user interface touchpad continuously tracks the victim, target or object despite movement of the Fire fighter and/or movement of the victim, target or object. Some embodiments comprise software to implement the display and communicate items on the augmented reality/virtual reality the method outlined above.

Some embodiments comprise dividing the scene into at least two portions wherein: a first portion of the scene is displayed with a first digital marking for the first user; and a second portion of the scene is displayed with a second digital marking for the second user. Some embodiments comprise determining a relative location of the first head display unit worn by the first user as compared to a second head display unit worn by a second user, determining the second head display unit's pointing direction and displaying a first digital line on the first head display unit wherein the digital line originates in proximity to the second head display unit and extends in the pointing direction of the second head display unit. Some embodiments comprise determining a look angle direction of a second user wearing a second head display unit with eye tracking capabilities and displaying a digital line on the first head display unit wherein the digital line originates in proximity to the second head display unit and extends in the look angle of the second user. Some embodiments comprise determining a convergence point of a second user in the scene and displaying a digital line on the first head display unit wherein the digital line originates in proximity to the second head display unit and extends to the convergence point of the second user. Some embodiments comprise determining a pointing direction of an object held by a second user and displaying a fourth digital line on the first head display unit wherein the fourth digital line originates in proximity to the second user and extends in the pointing of the object. Some embodiments comprise providing a first digital mark for a first item for the first user and providing a second digital mark for the first item for a second user. Some embodiments comprise providing a first set of digital marks to cause a first smooth tracking eye pattern for a first user and providing a second set of digital marks to cause a second smooth tracking eye pattern for a first user. Some embodiments comprise recording a first user's fixation locations of items in the scene and displaying at set of digital objects at the fixation locations. Some embodiments comprise displaying the set of digital objects to a second user. Some embodiments comprise placing a digital object in proximity to a moving item within the scene, which enables the first user to perform smooth tracking of the moving item. Some embodiments comprise placing an appearing-disappearing digital object in proximity to a moving item within the scene, which enables the first user to perform saccades of the moving item. Some embodiments comprise wherein the head display unit comprises at least one forward looking infrared camera and wherein an algorithm (e.g., artificial intelligence) uses the data from the at least one forward looking infrared camera to determine the optimum aim point for a fire hose and wherein the optimum aim point is displayed on the head display unit. Some embodiments comprise wherein the head display unit comprises a laser range finder and wherein the laser range finder generates a 3D image of the items and wherein a digital 3D image of the items is displayed on the head display unit to the first user.

Improved Effectiveness Via Artificial Intelligence Integration

Some embodiments comprise a method to apply artificial intelligence to enhance Fire fighter understanding of the fire situation and reaction thereto thereby increasing his/her effectiveness. Some embodiments comprise artificial intelligence software operating in the Fire fighter borne computer (or in the cloud) connected to and providing projections on a head mounted display and also connected to Fire fighter borne communications system to deliver artificial intelligence generated data over a tactical communications network. Some embodiments comprise a method of sequencing of fires across the team such that it has maximum impact on threat. Some embodiments comprise a method of optimizing fires across the team the assignment of targets to inflict greatest reduction of fire hazard. Some embodiments comprise a method to restructure the scheme of maneuver as the situation unfolds. Some embodiments comprise a method to react to newly received intelligence regarding a changed (or changing) threat situation. Some embodiments comprise a method to optimize questions to be asked during encounters with a victim during an operation as interrogation proceeds based on victim responses. Some embodiments comprise a method to analyze a person's gait and determination if the person is injured. Some embodiments comprise a method to determine the optimal aim point of a fire (e.g., an infrared camera can be utilized to determine the hottest source in the scene and from that determine the best location to hose down the fire). Some embodiments comprise a method to correlate data from team members for smart person counting. Some embodiments comprise a method to conduct terrain analysis for inter alia routes of approach and assignment of sectors. Some embodiments comprise software to implement artificial intelligence method outlined above. A key step is to perform a scene understanding process (such as is performed by the Microsoft HoloLens) on a head display unit wherein the scene contains a series of items. Next, perform eye tracking of a first user (e.g., Fire fighter) wearing the head display unit wherein the head display units has eye tracking capabilities and wherein the first user looks at at least one of the items. Next, analyzing the eye tracking data of the user. There are, however, several important additional features.

Some embodiments comprise developing and communicating among Fire fighter team members a method of sequencing of fire such that it has maximum impact on threat (e.g., all team members fire simultaneously at assigned targets rather than piecemeal wherein threat could take cover). Some embodiments comprise developing and communicating among Fire fighter team members a method of optimizing across the team the assignment of targets to inflict greatest effectiveness against the fire. Some embodiments comprise developing and communicating among Fire fighter team members a method to restructure the scheme of maneuver as the situation unfolds. Some embodiments comprise developing and communicating among Fire fighter team members a method to react to intelligence situation (e.g., wind shift). Some embodiments comprise developing and communicating among Fire fighter team members a method to optimize questions to be asked during encounters with a victim during an operation as interrogation proceeds based on victim responses. Some embodiments comprise developing and communicating among Fire fighter team members a method to analyze a persons gait and determination if a victim is injured. Some embodiments comprise developing and communicating among Fire fighter team members a method to determine the optimal aim point on the fire. Some embodiments comprise developing and communicating among Fire fighter team members a method to correlate data from team members for smart person counting (e.g., not double counting a person based on time, look angle, etc.). Some embodiments comprise developing and communicating among Fire fighter team members a method to conduct terrain analysis for inter alia: routes of approach; assignment of firing sectors; threat line-of-sight and associated hose coverage.

Improved Effectiveness Via Sensors

Some embodiments comprise wherein the first user's head display unit contains a first acoustic sensor and a first position locator and a second user's head display unit contains a second acoustic sensor and a second position locator and wherein data from the first user's head display unit and data from the second user's head display unit are utilized to triangulate the location of a sound. Some embodiments comprise wherein the first user's head display unit contains a hologram generator wherein a second user can view the hologram with the naked eye.

Some embodiments comprise an apparatus consisting of sensor systems and graphical user interface to enhance a Fire fighter's understanding of the actual fire situation or a training situation and reaction thereto thereby increasing his/her effectiveness. The apparatus would provide sensor data to software operating in the Fire fighter borne computer connected to and providing projections on a head mounted display and also connected to Fire fighter borne communications system to deliver artificial intelligence generated data over a tactical communications network. The preferred embodiment comprises: a 850 nm filter for a near IR sensor with associated capability to optionally display reverse polarity and apply and display aided target recognition cueing indicators; a milli-meter wave (MMW) capable of seeing thru walls and detecting concealed hoses; a forward looking infrared (FLIR) with flash detection capability; an acoustics sensors on helmet with: direction finding capability for source and type of sounds to include voice (e.g. of a victim) detection and location, capable of noise cancellation/sound enhancement and a capability to collect a composite collection of sounds from multiple team members to triangulate location of the voice (e.g., of a victim); a transmit/receive acoustics device to auditorily pass information and receive information from the Fire fighter; a multi-purpose eye-safe laser range finder and marker; a TV/FLIR with foreign language reading capability; a meteorological sensor system capable of determining temperature, wind direction and velocity and humidity. Some embodiments comprise software to integrate and leverage the capabilities of these sensors to generate, display and communicate items as described above. The leverage of sensors to enhance effectiveness of the Fire fighter will be through software comprising: aided target recognition and cueing applied to images obtained from sensor; flash detection (e.g., indicative of an explosion) applied to images; detection, classification and direction finding applied to acoustic data; enhanced target location accuracy through integration of sensor data; noise cancellation/sound enhancement applied to acoustic data; collection and creation of composite sounds data across members of the team applied to acoustic data; determine range to illuminated point based on data from sensor; combine data to compute hose elevation and angular pointing for fire engagement and target marking; apply foreign language reading to images from sensors; integration of data from the sensors to provide composite picture of the actual fire situation or training situation.

Some implementations comprise providing sensors and methods to implement a robust all weather Fire fighter borne sensor system. This includes, but is not limited to: (1) 850 nm filter for near IR sensor with associated capability to optionally display reverse polarity and apply and display aided target recognition (AiTR) for target cueing indicators (e.g., arrow, circle); (2) millimeter wave (MMW) to, inter alia, see thru walls by employing scanning feature; and identify victims; (3) FLIR with flash detection software; (4) acoustics sensors on helmet with: direction finding software for source and type of sound and type, AiTR (e.g., type vehicle, type language), shot detection with software for direction, distance, computation of GPS coordinates, noise cancellation/sound enhancement and, composite collection of sounds from multiple team members to triangulate location of a victim's voice; (5) TV/IR with foreign language reading capability; (6) meteorological sensor (e.g., wind, temperature); and (7) interface of sensors.

Some implementations comprise providing systems and methods to implement continuous collection of situational awareness. Some embodiments comprise wherein each team member record at some specified time interval relevant data from all sensors (e.g., GPS location; IR picture and look angle; acoustic recordings). Features include: software to generate composite picture over time; identification of suspicious persons; mental/health metrics as applied to Fire fighter over time.

Some implementations comprise providing systems and methods to implement targeting.

Some embodiments comprise target location system consisting of integration of input from the integration of integration of sensor data from inter alia: target cueing from 850 nm filtered near IR sensor data. Some embodiments comprise target location system consisting of integration of input from the integration of hyperspectral sensor data. Some embodiments comprise target location system consisting of integration of target location from own position, ESLRF, GPS direction or magnetic compass.

Some implementations comprise system control to enable the Fire fighter to operate the elements of the above system in a manner that he/she best accomplishes the mission in either a training or actual fire operation. Some embodiments comprise voice commands to change mode of system operation (e.g., issue command "range to target" and the system would respond by using the line where the Fire fighter were looking described in AR/VR portion, initiate the bore sighted multi-purpose laser, obtain range and display line and yard stick range on the head display, as a further example the voice command could be "menu" which would display various options).

Improved Effectiveness Via Situational Awareness

Some embodiments comprise implementing continuous collection of situational awareness to provide a record of Fire fighter location, activities health and mental status during operations in an actual fire situation or training situation. Continuous collection of situational awareness will be enabled through software operating in the Fire fighter borne computer connected to display unit and providing projections on a head mounted display and also connected to Fire fighter borne communications system to deliver continuous collection of situational awareness data over a tactical communications network comprising: for each team member, a record at some specified time interval relevant data from all sensors; hose data (e.g., volume, angle of spray, target, etc.) to include time and location of Fire fighter hose; images of victims; mental/health metrics over time; teammate and potential victim tracking data in specified zone; other activities as specified in unit standard operating procedures. Some embodiments comprise software to implement continuous collection of situational awareness methods outline to generate, display and communicate items as described above.

Some embodiments comprise a method for improved item tracking. A key innovative step in this is the registering a digital volume-subtending 3D cursor to an item wherein the shape of the 3D cursor comprising a three-dimensional geometric object and a halo surrounding the item.

Improved Effectiveness Via Control Methods

A method of system control methods, apparatuses and software to enable the Fire fighter to operate the elements of the above system in a manner that he/she best accomplishes the mission in either a training or real life operation. This control method includes, but is not limited to: voice commands to change mode of system operation be "menu" which would display various options; cursor(s) to, inter alia, mark a victim, target or object or interact with system control through Fire fighter interaction with graphical user interface touchpad or surface; interaction between either the voice commands and/or the cursor to change the system mode of operation. A receive antenna for voice commands. Some embodiments comprise software to implement system control of elements to generate, display and communicate tasks.

Some embodiments comprise a method for improved inputs. The preferred embodiment is for a camera to be placed on a camera in a position where it can visualize the user's hands touching an object. The preferred embodiment is for the object to be the desk. Other embodiments can include the user's thighs. Consider the example of the user's thighs. A user's left hand is located on the first user's left thigh. The user's right hand is located on the first user's right thigh. The user's left hand, right hand, left thigh and right thigh are within a camera's field of view. A movement of a finger of the user's right hand causes a first digital action (such as a keystroke). A movement of a finger of the user's left hand causes a second digital keystroke. This is an improvement over the prior art because the user's head could be in a relaxed, forward position and the user's hands could be in a downward, relaxed position. This removes neck strain. Further, there is some tactile feedback from touching the surface. Some embodiments comprise wherein a movement comprises a tapping motion, a lifting motion, and a dragging motion. Some embodiments comprise wherein the determination of which keystroke is determined by at least one of the group consisting of: a position of a finger on a thigh; a speed of a finger movement; and an artificial intelligence algorithm.

Some implementations comprise system control to enable the Fire fighter to operate the elements of the above system in a manner that he/she best accomplishes the mission in either a training or actual situation. This includes, but is not limited to: (1) voice commands to change mode of system operation (e.g., issue command "range to target" and the system would respond by using the line where the Fire fighter were looking described in AR/VR portion, initiate the bore sighted multi-purpose laser, obtain range and display line and yard stick range on the head display, as a further example the voice command could be "menu" which would display various options); (2) a cursor to mark a victim, target or object or interact with system control through Fire fighter interaction with graphical user interface touchpad; (3) interaction between either the voice commands and/or the cursor to change the system mode of operation. Some embodiments comprise a method to apply a targeting capability to enhance Fire fighter increase probability of hit and accuracy and timeliness of calls for fire(s) in an actual fire situation or training and thereby increasing his/her effectiveness. Targeting capability will be implemented through software operating in the Fire fighter borne computer. Additionally, a head mounted display also connected to Fire fighter borne communications system to deliver targeting data over a tactical communications network will be utilized. A target location system comprises integration of input from the following: integration of sensor data; cues by other Fire fighter sensor systems; determine target location relative to own position via a eye-safe laser range finder (ESLRF), GPS direction finding and magnetic compass; multi-function ESLRF: targeting mode with a digital object based on range and meteorological data and places a digital object on location on the location where the Fire fighter should be aiming. Some embodiments comprise software to implement targeting methods to generate, display and communicate items as described above.

Increased Survivability

An apparatus to implement protective measures to enhance Fire fighter survivability in an actual fire event and in training and thereby increasing his/her effectiveness. Implementation of protective measures will be through software operating in the Fire fighter borne computer connected apparatus items listed below and providing projections on a head mounted display and also connected to Fire fighter borne communications system to deliver data over a tactical communications network. Some embodiments comprise utilization of a femto-second lasers with the capability to create series of series of flashes offset the user confuse to create holograms to serve as an alert to others of a user's position.

Some embodiments comprise a method to implement protective measures to enhance Fire fighter survivability in a real life or training situation and thereby increasing his/her effectiveness. Implementation of protective measures will be through software operating in the Fire fighter borne computer connected apparatus and providing projections on a head mounted display and also connected to Fire fighter borne communications system to deliver data over a tactical communications network. This is useful because a master fire fighter can lead the efforts in a better way and be able to better manage risk of fire fighters, better save lives of victims and better take out the fire.

Morale Boost

A method to support and improve morale to enhance Fire fighter performance in an actual or training actual fire and thereby increasing his/her effectiveness. Implementation of morale improvement techniques will be through software operating in the Fire fighter borne computer connected to the apparatus and providing projections on a head mounted display and also connected to Fire fighter borne communications system to deliver data over a tactical communications network. Morale improvement techniques methods comprising of the following: provide music to inspire before a mission (e.g., Rocky on steps of museum in Philly), provide movies, music, internet, etc. during rest periods; provide continuous monitoring of key health metrics inter alia pulse rate, temperature; provide comparison to standardized metrics and when body in danger zone send message to leader and medic; and, provide trauma detection and generate message alerting medical evacuation in accordance with unit standard operating procedures.

BRIEF DESCRIPTION OF FIGURES

FIG. 5E illustrates a 3D picture-in-picture type display wherein a first user can see what a second user is looking at.

FIG. 7A illustrates the head display unit showing use of a saccades visual aid marker.

FIG. 7B illustrates a flow chart to supplement FIG. 7A.

DETAILED DESCRIPTION OF FIGURES

Figure 1:
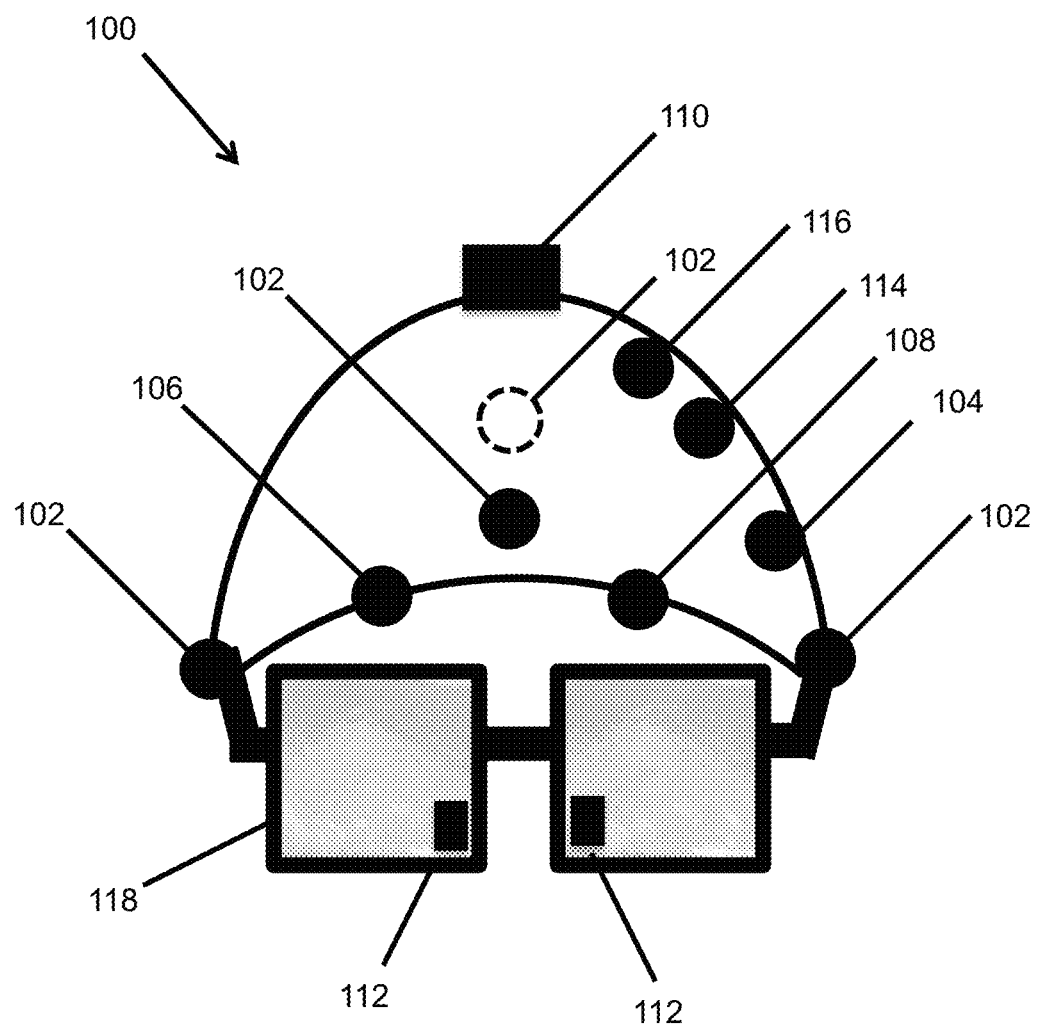
FIG. 1 illustrates a Fire fighter head display unit.

FIG. 1 illustrates a Fire fighter head display unit. 100 illustrates the head display unit, which in this embodiment is in the form of a helmet with sensors mounted on the helmet. Multiple acoustic sensors 102 are shown, one for each quadrant. A multipurpose laser range finder/marker 104 is shown. A forward looking infrared (FLIR)/TV 106 is shown. A near-infrared (IR) (preferred embodiment is 850 mm) unit 108 is shown. A hologram generator 110 is shown. An eye tracking system 112 is shown. The eye tracking is important for a variety of aspects of this patent. For example, assessing alertness, enhancing viewing during the human eye's smooth tracking and saccades movements and alerting a first user where a second user is looking. A digital magnetic compass 114 is shown. A laser receiver 116 is shown. An extended reality unit is shown 118.

Figure 2:
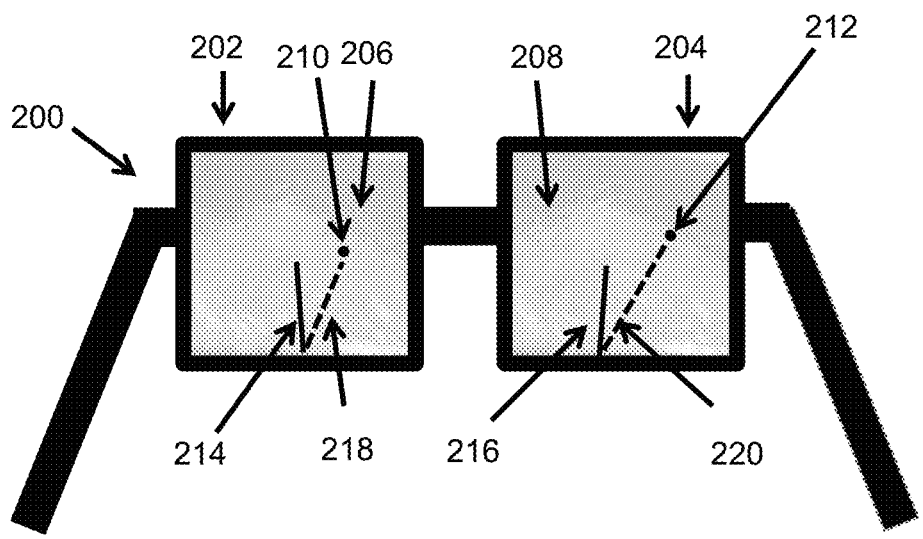
FIG. 2 illustrates the head display unit showing digital lines.

FIG. 2 illustrates the head display unit showing digital lines. The head display unit 200 is shown, which contains a left eye display 202 and a right eye display 204. A Fire fighter can see a left eye view of the terrain 206 and a right eye view of the terrain 208. The convergence point in the left eye display 210 is shown. The convergence point in the right eye display 212 is also shown. Please see U.S. Pat. No. 9,349,183, METHOD AND APPARATUS FOR THREE DIMENSIONAL VIEWING OF IMAGES, which is incorporated by reference in its entirety, for additional details regarding convergence. In the left eye display 202, there is a first digital line 214 illustrating the pointing direction of the user's head display unit. In the right eye display 204, there is a second digital line 216 illustrating the pointing direction of the user's head display unit. In the left eye display 202, there is a third digital line 218 illustrating the look angle of the left eye, which goes to convergence point 210. In the right eye display 204, there is a fourth digital line 220 illustrating the look angle of the right eye, which goes to convergence point 212. Note that this figure illustrates lines where the user is looking. However, other digital objects other than lines (e.g., dots) can be utilized. Furthermore, as taught later in this patent, the digital lines that are displayed on a first user's head display unit could be of a second user. Furthermore, a composite line displaying the general HDU pointing directions or look angles could also be utilized if one person was trying to determine in general where a group of users is looking.

Figure 3:
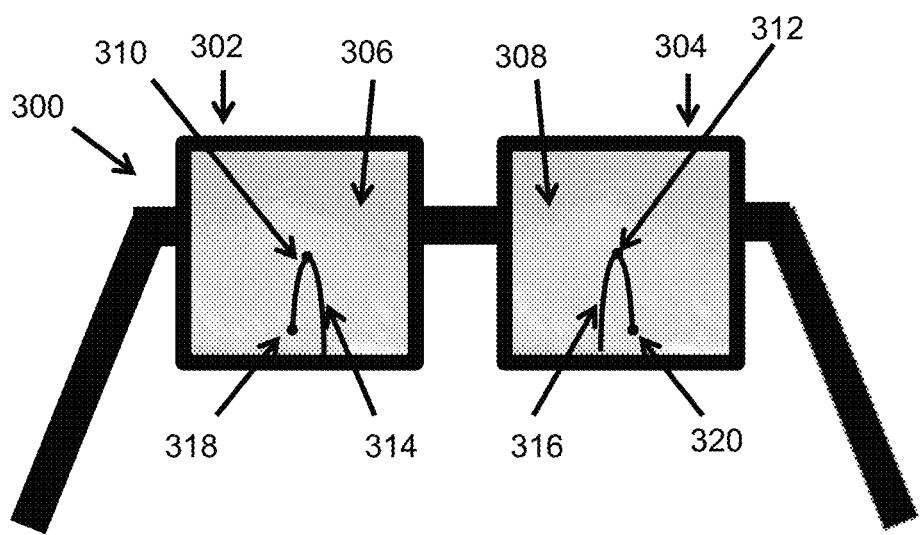
FIG. 3 illustrates the head display unit showing a simulated line of fire of hose.

FIG. 3 illustrates the head display unit showing a simulated line of fire of hose. The head display unit 300 is shown, which contains a left eye display 302 and a right eye display 304. Wearing the head display unit 300, the Fire fighter can see a left eye view of the terrain 306 and a right eye view of the terrain 308. The aim point of the user's hose in the left eye display 310 is shown. The aim point of the user's hose in the right eye display 312 is also shown. 314 illustrates the trajectory of the water (or other fire repellant) stream through the air in the left eye field of view. 316 illustrates the trajectory of the water (or other fire repellant) stream through the air in the right eye field of view. 318 illustrates the spot where the water (or other fire repellant) hits the target on the left eye field of view. 320 illustrates the spot where the water (or other fire repellant) hits the target on the left eye field of view. Note that hash marks can be used along the trajectories to show distance markers. The system improves performance by adding a target, which can adjust for a variety of factors (e.g., distance, wind, weapon type, etc.) to assist with aiming.

Figure 4:
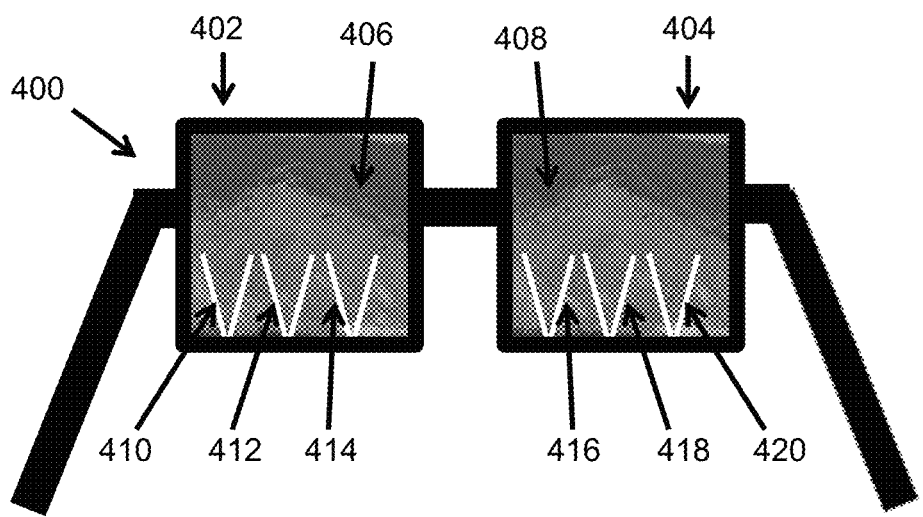
FIG. 4 illustrates the head display unit showing coordination between sectors of spray of water or fire repellant.

FIG. 4 illustrates the head display unit showing coordination between sectors of spray of water or fire repellant. The head display unit 400 is shown, which contains a left eye display 402 and a right eye display 404. Through the lenses of the head display unit 400, the Fire fighter can see a left eye view of the scene 406 and a right eye view of the scene 408. The left eye view of simulated line pair 410 (in a "V" shape) designating a first teammate's sector of hosing. The left eye view of simulated line pair 412 (in a "V" shape) designating the sector of fire of the Fire fighter who is viewing the HDU 400 shown in this image. The left eye view of simulated line pair 414 (in a "V" shape) designating a second teammate's sector of hosing. The right eye view of simulated line pair 416 (in a "V" shape) designating a first teammate's sector of hosing. The right eye view of simulated line pair 418 (in a "V" shape) designating the sector of fire of the Fire fighter who is viewing the HDU 400 shown in this image. The right eye view of simulated line pair 420 (in a "V" shape) designating a second teammate's sector of hosing.

Figure 5A:
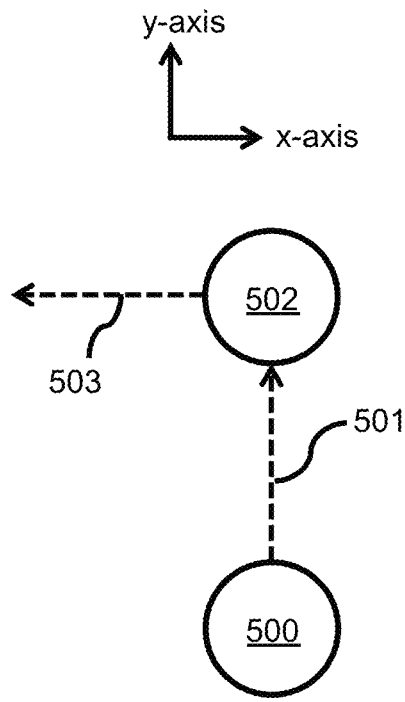
FIG. 5A illustrates a top down view of two fire men.

FIG. 5A illustrates a top down view of two fire men. 500 illustrates a first Fire fighter. 501 illustrates the pointing direction of the first Fire fighter's head display unit. 502 illustrates a second Fire fighter. 503 illustrates the pointing direction of the second Fire fighter's head display unit. For illustrative purposes, the x-axis and y-axis are shown. Assume that the second Fire fighter 502 and the first Fire fighter 500 are 500 feet away from one another and it is too far for the First fire fighter 500 to see the detail of the second Fire fighter 502, but the first Fire fighter 500 wants to know where the second Fire fighter is looking.

Figure 5B:
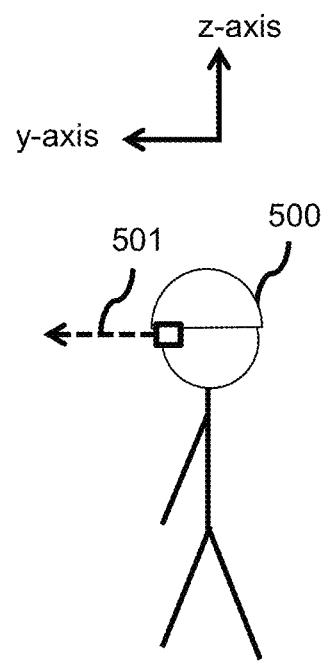
FIG. 5B illustrates a cross sectional view of the first Fire fighter in the y-z plane.

FIG. 5B illustrates a cross sectional view of the first Fire fighter in the y-z plane. 500 illustrates the first Fire fighter. 501 illustrates the pointing direction of the first Fire fighter's head display unit. For illustrative purposes, the y-axis and z-axis are shown.

Figure 5C:
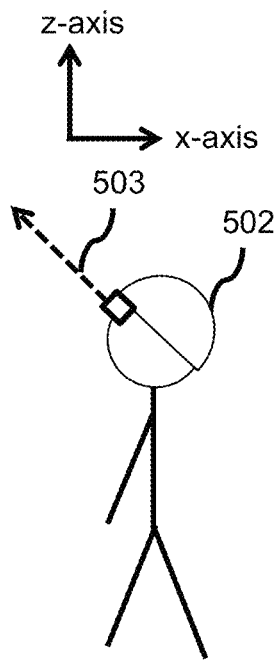
FIG. 5C illustrates a cross sectional view of the second Fire fighter in the x-z plane.

FIG. 5C illustrates a cross sectional view of the second Fire fighter in the x-z plane. 500 illustrates the second Fire fighter. 503 illustrates the pointing direction of the second Fire fighter's head display unit. For illustrative purposes, the x-axis and z-axis are shown.

Figure 5D:
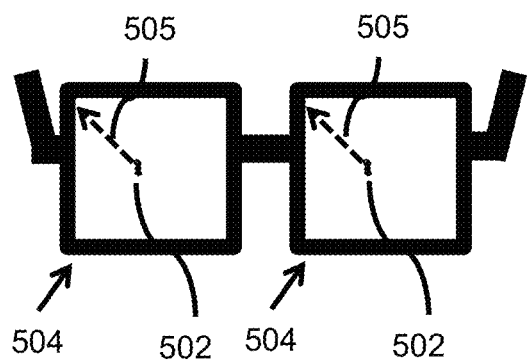
FIG. 5D illustrates what the first fire fighter would see when looking at the second fire fighter.

FIG. 5D illustrates what the first fire fighter would see when looking at the second fire fighter. 504 illustrates the head display unit of the first Fire fighter. 502A illustrates the second Fire fighter in the right eye display. 502B illustrates the second Fire fighter in the right eye display. 505A illustrates a digital line displayed on the right eye portion of the head display unit of the first Fire fighter, which corresponds to the pointing direction of the second Fire fighter, which is shown as 503 in FIGS. 5A and 5C. This simple scenario is meant to illustrate the inventive step. In practice, the change in height, change in forward position, change in side position, change in pointing direction are accounted for in real time. Note that this was shown for the pointing direction of the HDU; however, it could be shown for the look angle or via the aim direction (e.g., of the fire hose).

Figure 5E:
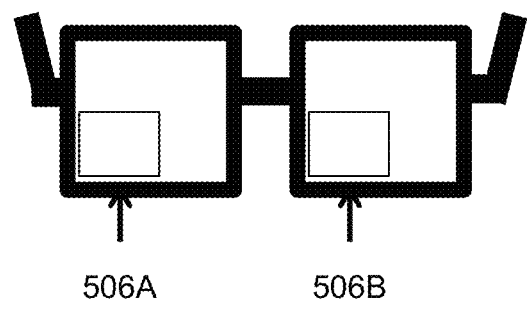

FIG. 5E illustrates a 3D picture-in-picture type display wherein a first user can see what a second user is looking at. 506A illustrates what user 502 is viewing in the left eye display. 506B illustrates what user 502 is viewing in the right eye display. Thus, this would be a 3D picture in picture.

Figures 6A, 6B:
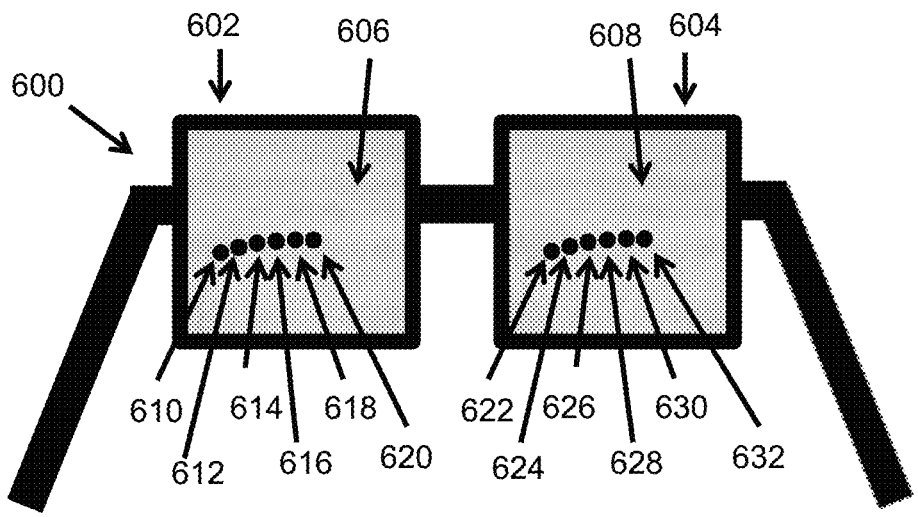
FIG. 6A illustrates the head display unit showing use of a smooth tracking visual aid marker.
FIG. 6B illustrates a flow chart to supplement FIG. 6A.

FIG. 6A illustrates the head display unit showing use of a smooth tracking visual aid marker. The head display unit 600 is shown, which contains a left eye display 602 and a right eye display 604. Through the lenses of the head display unit 600, the Fire fighter can see a left eye view of the terrain 606 and a right eye view of the terrain 608. A left eye view of the smooth tracking visual aid marker is shown at a first time point 610, a second time point 612, a third time point 614, a fourth time point 616, a fifth time point 618 and a sixth time point 620. A right eye view of the smooth tracking visual aid marker is shown at a first time point 622, a second time point 624, a third time point 626, a fourth time point 628, a fifth time point 630 and a sixth time point 632. The visual aid marker can take multiple shapes, sizes, colors and visual appearances, such as a round circle, arrow, etc. The data received would be uploaded into the continuous situational awareness system. Multiple Fire fighters could see the same marker (from different view points). This is useful because there may be something in the field of view of interest (e.g., victim) that is slowly moving, but hard to see. The visual tracker helps identify such an item. FIG. 6B illustrates a flow chart to supplement FIG. 6A. In the first step 634, some situations, the camera can detect small movements of an item of interest that the human eye does not detect or does not detect very well. Next 636, the HDU display can place a smooth tracking dot in close proximity to a small moving object. Finally 638, the smooth tracking dot moves in a continuous fashion so as to help the human eye follow the subtle movement.

FIG. 7A illustrates the head display unit showing use of a saccades visual aid marker. The head display unit 700 is shown, which contains a left eye display 702 and a right eye display 704. Through the lenses of the head display unit 700, the Fire fighter can see a left eye view of the terrain 706 and a right eye view of the terrain 708. In this scenario, there are three items are need to be tracked by a single Fire fighter. It is easy for a Fire fighter to forget one of the targets.

Therefore, this technique is useful. A left eye view of a first saccadian tracking visual aid marker 710 is shown during a first time interval (e.g., time interval between 0 seconds and 2 seconds), but subsequently disappears (e.g., immediately after the 0 seconds to 2 seconds time interval has passed). A left eye view of a second saccadian tracking visual aid marker 712 is shown during a second time interval (e.g., time interval between 2 seconds and 4 seconds), but subsequently disappears (e.g., immediately after the 2 seconds to 4 seconds time interval has passed). A left eye view of a third saccadian tracking visual aid marker 714 is shown during a third time interval (e.g., time interval between 4 seconds and 6 seconds), but subsequently disappears (e.g., immediately after the 4 seconds to 6 seconds time interval has passed). A right eye view of a first saccadian tracking visual aid marker 716 is shown during a first time interval (e.g., time interval between 0 seconds and 2 seconds), but subsequently disappears (e.g., immediately after the 0 seconds to 2 seconds time interval has passed). A right eye view of a second saccadian tracking visual aid marker 718 is shown during a second time interval (e.g., time interval between 2 seconds and 4 seconds), but subsequently disappears (e.g., immediately after the 2 seconds to 4 seconds time interval has passed). A right eye view of a third saccadian tracking visual aid marker 720 is shown during a third time interval (e.g., time interval between 4 seconds and 6 seconds), but subsequently disappears (e.g., immediately after the 4 seconds to 6 seconds time interval has passed). This process would then repeat so the Fire fighter would repeat monitoring of the items. For example, a left eye view of a first saccadian tracking visual aid marker 710 is shown during a fourth time interval (e.g., time interval between 6 seconds and 8 seconds), but subsequently disappears (e.g., immediately after the 6 seconds to 8 seconds time interval has passed) and a right eye view of a first saccadian tracking visual aid marker 716 is shown during a fourth time interval (e.g., time interval between 6 seconds and 8 seconds), but subsequently disappears (e.g., immediately after the 6 seconds to 8 seconds time interval has passed). And so on. The saccadian tracking visual aid marker (e.g., circle shown in this figure) can take multiple shapes, sizes, colors and visual appearances, such as an arrow, etc. The data received would be uploaded into the continuous situational awareness system. Multiple troops could see the same marker. FIG. 7B illustrates a flow chart to supplement FIG. 7A. In the processing block 722, some situations require that multiple objects need to be tracked by a single Fire fighter. And, of course, the Fire fighter is vulnerable to human error and improper sequencing and tracking. In the second step 724, the HDU displays a first saccadian visual aid marker at the first object for a first time interval, a second saccadian visual aid marker at a second object during a second time interval. And, so on. Finally, the saccadian visual aid marker described in processing block 724 repeats for additional rounds. Combinations of smooth tracking visual aid markers (e.g., shown continuously or shown for specific intervals) and saccadian visual aid markers would optimize a Fire fighter's ability to monitor multiple targets.

Figure 8:
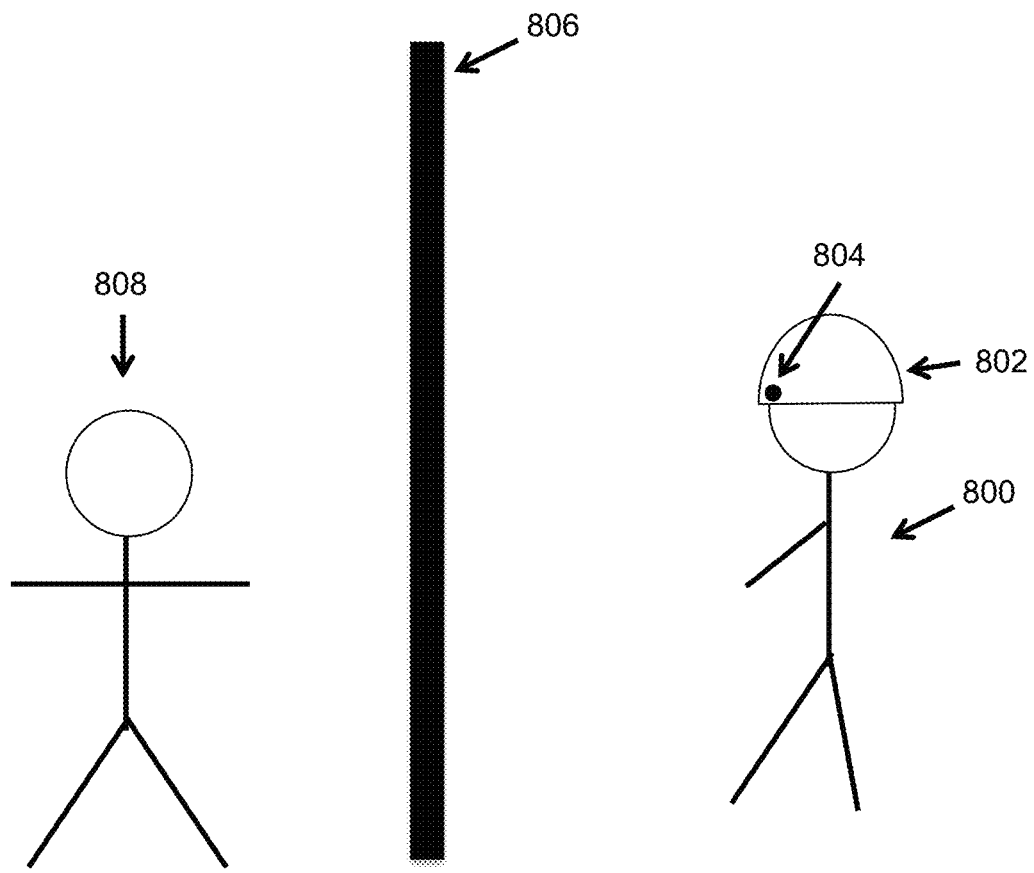
FIG. 8 illustrates use of a milli-meter wave (MMW) to help the Fire fighter see through walls.

FIG. 8 illustrates use of a milli-meter wave (MMW) to help the Fire fighter see through walls. A Fire fighter 800 is shown wearing a helmet 802 equipped with MMW 804. A wall 806 is shown. A victim 808 are shown hidden behind the wall. The MMW sensor 804 on the helmet 802 can detect the victim 808, which can be displayed on the head display unit (not shown). The preferred MMW is available at Intelligent Automation Incorporated, Rockville, Md.

Figure 9:
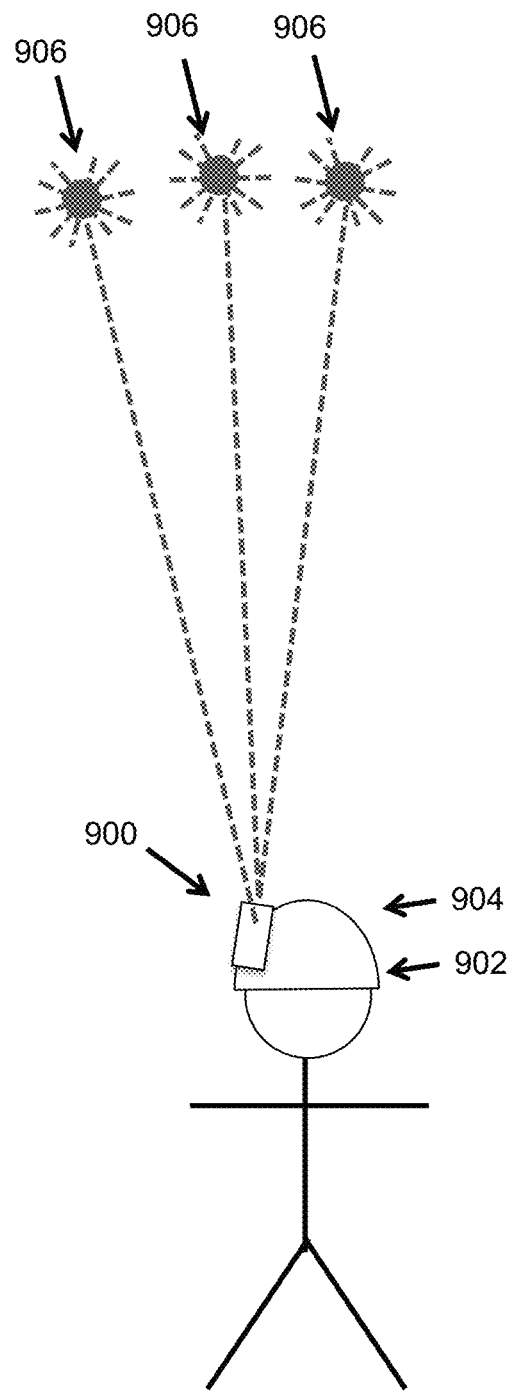
FIG. 9 illustrates generation of multiple holographic flashes.

FIG. 9 illustrates generation of multiple holographic flashes. A Fire fighter 900 is shown wearing a helmet 902 equipped with a holographic generator 904. The holographic generator (e.g., femtosecond laser hologram) 904 emits pulses to simulate flashes 906. This can serve as a notification of a position of the Fire fighter to other individuals (not wearing a HDU). In some embodiments, a police officer could use this apparatus to help disperse crowds. For example, one police officer could generate images of many police officers as a scare tactic. In some embodiments, this could be used for entertainment (e.g., generation of Disney characters).

Figure 10:
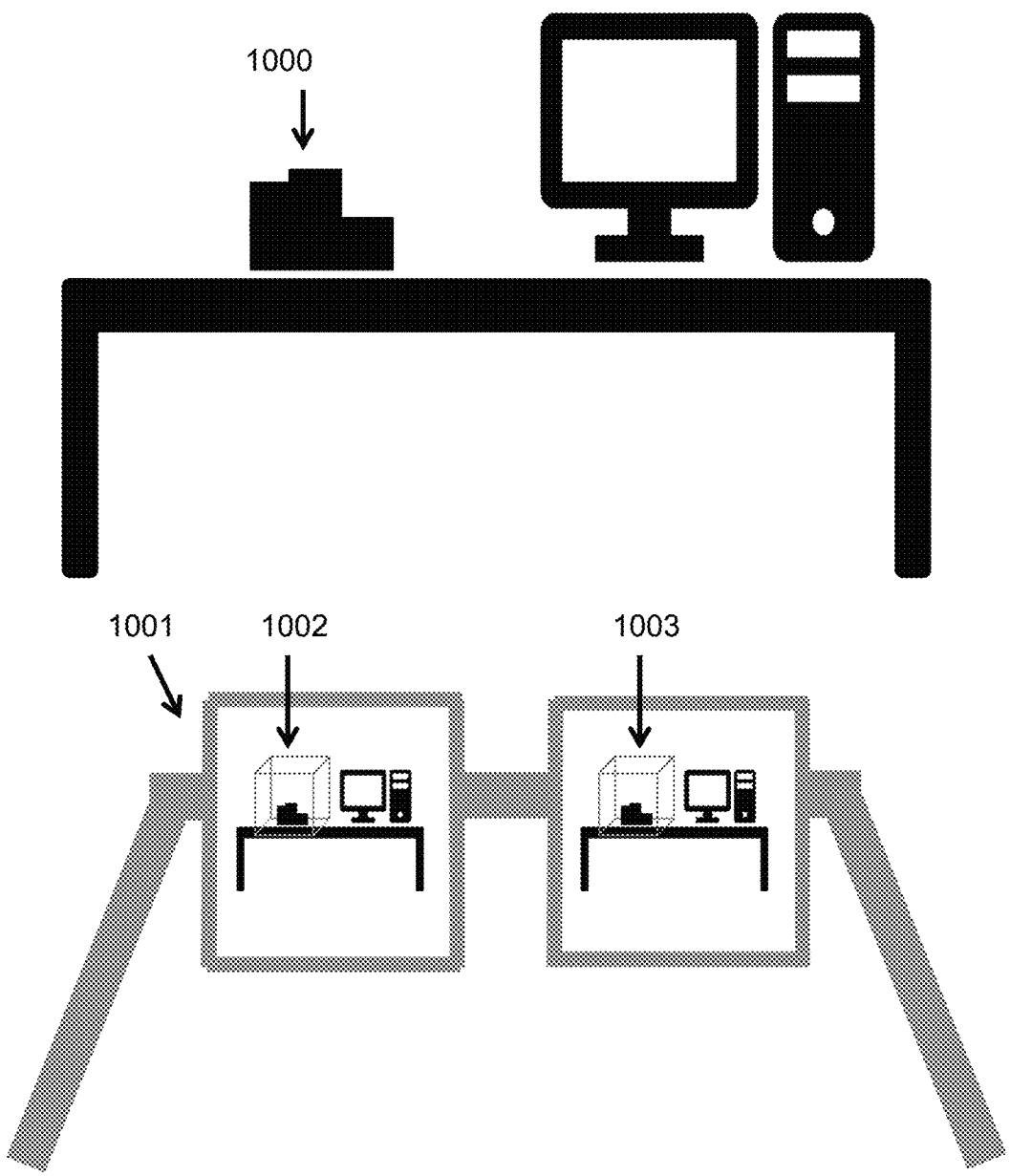
FIG. 10 illustrates the placement of a digital 3D cursor into the physical world.

FIG. 10 illustrates the placement of a digital 3D cursor into the physical world. 1000 illustrates an object on a desk. 1001 illustrates an extended reality display wherein the extended reality glasses show the objects on the desk as well as the 3D cursor surrounding the object 1000. 1002 illustrates the 3D cursor in the left eye display. 1003 illustrates the 3D cursor in the right eye display. Thus, this embodiment comprises a 3D cursor can be placed onto a physical object. For example, in the event of a prolonged rescue situation, certain items need to be accounted for at all times (e.g., oxygen tank). This embodiment discloses a method of placing a 3D cursor around the physical items. The 3D cursor could take the form of a 3D geometric object or a halo surrounding the item. The placement of the 3D cursor could be via hand gestures, tool or voice command. The user could implement a command to show or hide all 3D cursors. This could be helpful for object tracking. Additional description of the 3D cursor is disclosed in METHOD AND APPARATUS FOR THREE DIMENSIONAL VIEWING OF IMAGES, U.S. Pat. No. 9,980,691, which is incorporated by reference in its entirety. Additionally, features include those described in U.S. patent application Ser. No. 16/785,606, IMPROVING IMAGE PROCESSING VIA A MODIFIED SEGMENTED STRUCTURE, which is incorporated by reference in its entirety. In other non-fire fighter example, this could represent a concept of a family who has a housekeeper. The family needs the kitchen to be cleaned, but there are so many areas in the kitchen. The housekeeper needs to know which areas to focus on. Therefore, the family could indicate high priority areas by placing a series of volume cursors over the areas (e.g., oven, toaster, dishwasher, etc.). Medium and low priority areas could be marked in a similar manner.

Figure 11A:
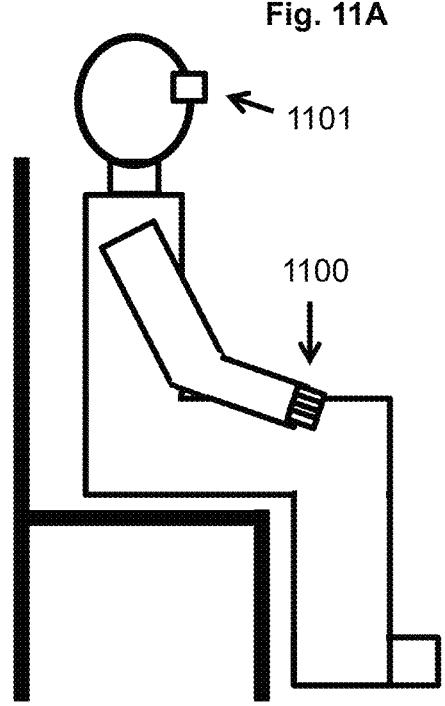
FIG. 11A illustrates a user who is using their thighs as a surface to type.

FIG. 11A illustrates a user who is using their thighs as a surface to type. 1100 illustrates the hands of a user which are touching the user's thighs. Note that touching the thighs is preferred because the user would have tactile sensation from both the skin on the thighs and the finger tips. 1101 illustrates the head display unit.

Figure 11B:
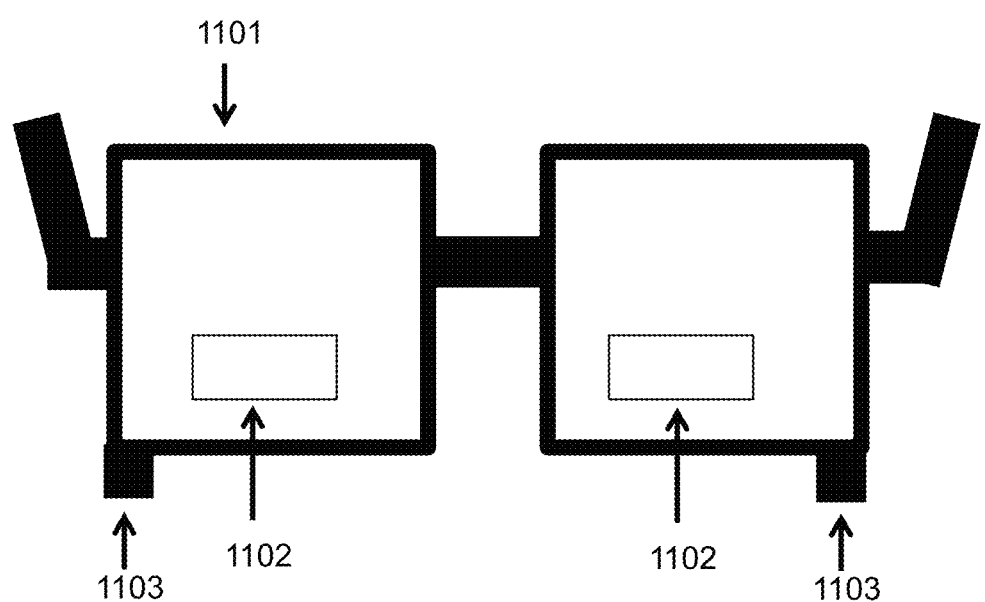
FIG. 11B illustrates what the user sees on their head display unit while typing.

FIG. 11B illustrates what the user sees on their head display unit while typing. 1101 illustrates the head display unit. 1102 illustrates a digital keyboard on the head display unit. 1103 illustrates downward facing cameras, which show the user's hands while they are on the user's lap.

What is claimed is:
1. A method comprising:
   performing scene understanding of an image of a physical scene obtained from a sensor system on a head display unit
   wherein the physical scene contains physical items,
   wherein said image contains structures,
   wherein said structures correspond to said physical items,
   wherein said scene understanding comprises segmentation of said image into segmented structure(s);

displaying said image on said head display unit;
performing eye tracking of a first user's eye movements while said first user is wearing the head display unit wherein the head display unit has eye tracking capabilities, and
wherein the first user visualizes at least one of said segmented structures which corresponds to at least one of the physical items; and
analyzing eye tracking data of the first user to determine which segmented structure(s) said first user has viewed.

2. The method of claim 1 further comprising:
generating a digital object to designate segmented structures that are not detected; and
displaying said digital object on said head display unit.

3. The method of claim 1 further comprising:
determining a relative location of the head display unit worn by the first user as compared to a second head display unit worn by a second user;
determining the second head display unit's pointing direction; and
displaying a digital line on the first head display unit wherein the digital line originates in proximity to the second head display unit and extends in the pointing direction of the second head display unit.

4. The method of claim 1 further comprising:
determining a look angle direction of a second user wearing a second head display unit with eye tracking capabilities;
displaying a digital line on the head display unit wherein the digital line originates in proximity to the second head display unit and extends in the look angle of the second user.

5. The method of claim 1 further comprising:
determining a convergence point of a second user in the scene;
displaying a digital line on the head display unit wherein the digital line originates in proximity to the second head display unit and extends to the convergence point of the second user.

6. The method of claim 1 further comprising:
determining a pointing direction of an object held by a second user; and
displaying a digital line on the head display unit wherein the digital line originates in proximity to the second user and extends in the pointing direction of the object.

7. The method of claim 1 further comprising:
performing an aided target recognition (AiTR) of said segmented structure(s) within said image.

8. The method of claim 7 further comprising:
wherein if said AiTR determines that a segmented structure is a target, providing an alert to said first user wherein said alert comprises a visual alert, an audio alert or a tactile alert.

9. The method of claim 1 further comprising:
determining said first user's fixation location of a physical item in said scene comprising:
using said first user's GPS,
using said first user s laser range finder, and
using said first user's digital compass, and
recording said first user's fixation location of said physical item in said scene.

10. The method of claim 9 further comprising:
performing an aided target recognition (AiTR) of said segmented structure at said first user's fixation location,
recording results of said AiTR; and
passing results of said AiTR and said first user's fixation location to a second user.

11. The method of claim 1 further comprising placing a digital object on said head display unit in proximity to a moving physical item within the scene, which enables the first user to perform smooth tracking of the moving physical item.

12. The method of claim 1 further comprising placing an appearing-disappearing digital object on said head display unit in proximity to a moving physical item within the scene, which enables the first user to perform saccades of the moving physical item.

13. The method of claim 1 further comprising wherein the head display unit comprises at least one forward looking infrared camera and wherein an artificial intelligence algorithm uses the data from the at least one forward looking infrared camera to determine the optimum aim point for a fire hose and wherein the optimum aim point is displayed on the head display unit.

14. The method of claim 1 further comprising wherein the head display unit comprises a laser range finder and wherein the laser range finder generates a 3D image of the physical items and wherein a digital 3D image of the physical items is displayed on the head display unit to the first user.

15. The method of claim 1 further comprising wherein the first user's head display unit contains a first acoustic sensor and a first position locator and a second user's head display unit contains a second acoustic sensor and a second position locator and wherein data from the first user's head display unit and data from the second user's head display unit are utilized to triangulate the location of a sound.

16. The method of claim 1 further comprising wherein the first user's head display unit contains a hologram generator wherein a second user can view a hologram generated by said hologram generator with the his or her naked eye.

17. The method of claim 1 further comprising
wherein the first user's left hand is located on the first user's left thigh;
wherein the first user's right hand is located on the first user's right thigh;
wherein the first user's left hand, right hand, left thigh and right thigh are within a camera's field of view;
wherein a movement of a finger of the user's right hand causes a first digital keystroke; and
wherein a movement of a finger of the user's left hand causes a second digital keystroke.

18. The method of claim 17 further comprises wherein a movement comprises a tapping motion, a lifting motion, or a dragging motion.

19. The method of claim 17 further comprises wherein a keystroke is determined by at least one of the group consisting of:
a position of a finger on a thigh;
a speed of a finger movement; and
an artificial intelligence algorithm.

20. A system comprising:
a head display unit (HDD) with a left eye display and a right eye display;
an eye tracking system configured to track a left eye of a user and a right eye of said user,
a sensor system mounted on said HDU comprising at least one of:
a camera system;
a forward looking infrared (FLIR) sensor;
a laser range finder;
a digital compass;
a GPS; and
acoustic sensor(s);

a processor wherein the processor performs processing comprising:
- performing scene understanding of an image of a physical scene obtained from said sensor system
  - wherein the physical scene contains physical items,
  - wherein said image contains structures,
  - wherein said structures correspond to said physical items,
  - wherein said scene understanding comprises segmentation of said image into segmented structure(s);
- performing eye tracking of said user s eye movements while said user is wearing the head display unit
  - wherein the head display unit has eye tracking capabilities, and
  - wherein said user visualizes at least one of the physical items; and
- analyzing eye tracking data of said user to determine which segmented structure(s) said user has viewed.

\* \* \* \* \*